(12) United States Patent
Wang et al.

(10) Patent No.: US 8,436,217 B2
(45) Date of Patent: May 7, 2013

(54) INTEGRATED PROCESS TO CO-PRODUCE 1,1,1,3,3-PENTAFLUOROPROPANE, TRANS-1-CHLORO-3,3,3-TRIFLUOROPROPENE AND TRANS-1,3,3,3-TETRAFLUOROPROPENE

(75) Inventors: Haiyou Wang, Amherst, NY (US); Daniel C. Merkel, Orchard Park, NY (US); Konstantin A. Pokrovski, Orchard Park, NY (US); Hsueh Sung Tung, Getzville, NY (US); Ian Shankland, Randolph, NJ (US)

(73) Assignee: Honeywell International Inc., Morristown, NJ (US)

( * ) Notice: Subject to any disclaimer, the term of this patent is extended or adjusted under 35 U.S.C. 154(b) by 80 days.

(21) Appl. No.: 13/093,007

(22) Filed: Apr. 25, 2011

(65) Prior Publication Data

US 2012/0271070 A1 Oct. 25, 2012

(51) Int. Cl.
*C07C 17/25* (2006.01)
*C07C 19/08* (2006.01)
*C07C 21/18* (2006.01)
*C07C 23/00* (2006.01)
*C07C 25/00* (2006.01)
*C07C 17/00* (2006.01)

(52) U.S. Cl.
USPC ............ 570/158; 570/151; 570/153; 570/155

(58) Field of Classification Search .................. None
See application file for complete search history.

(56) References Cited

U.S. PATENT DOCUMENTS

| | | | | |
|---|---|---|---|---|
| 5,710,352 | A * | 1/1998 | Tung .............................. | 570/166 |
| 6,521,802 | B1 | 2/2003 | Takubo et al. | |
| 6,548,720 | B2 * | 4/2003 | Manogue et al. ............. | 570/157 |
| 6,844,475 | B1 * | 1/2005 | Tung et al. .................... | 570/168 |
| 2007/0238908 | A1 | 10/2007 | Merkel et al. | |
| 2008/0051611 | A1 | 2/2008 | Wang et al. | |
| 2011/0245549 | A1 | 10/2011 | Merkel et al. | |
| 2012/0059200 | A1 | 3/2012 | Pokrovski et al. | |

FOREIGN PATENT DOCUMENTS

| | | |
|---|---|---|
| CN | 101028992 A | 5/2007 |
| CN | 101028993 A | 5/2007 |
| CN | 101050162 A | 10/2007 |
| DE | 19716337 A1 | 11/1997 |
| GB | 2313118 A | 11/1997 |
| WO | 9812161 A1 | 3/1998 |
| WO | 9821171 A1 | 5/1998 |
| WO | 0140151 A1 | 6/2001 |
| WO | 2010035748 A1 | 4/2010 |
| WO | WO-2010059496 * | 5/2010 |

OTHER PUBLICATIONS

Quan, Heng-Dao, et al., Preparation of 1,1,1,3,3-pentafluoropropane (HFC-245fa) by using a SbF5-attached catalyst, Journal of Fluorine Chemistry, 2007, pp. 190-195, vol. 128, No. 3.
PCT ISR & Written Opinion issued in PCT/US2012/033419 dated Dec. 26, 2012.

* cited by examiner

*Primary Examiner* — Sudhakar Katakam
*Assistant Examiner* — Clinton Brooks
(74) *Attorney, Agent, or Firm* — Bruce O. Bradford

(57) ABSTRACT

Disclosed is a fully integrated process for making 1,1,1,3,3-pentafluoropropane (HFC-245fa), trans-1-chloro-3,3,3-trifluoropropene (HCFO-1233zd(E)), and trans-1,3,3,3-tetrafluoropropene (HFO-1234ze(E)). The chemistry involves (a) the reaction of 1,1,1,3,3-pentachloropropane (HCC-240fa), or a derivative thereof selected from 1,1,3,3-tetrachloropropene and 1,3,3,3-tetrachloropropene, with anhydrous HF in excess in the presence of a catalyst in a liquid-phase reactor in such a way as to co-produce HCFO-1233zd, HFO-1234ze, HCFC-244fa (3-chloro-1,1,1,3-tetrafluoropropane), and HFC-245fa in a first reactor; (b) the reaction of HCFO-1233zd and HFO-1234ze with HCl in excess in the presence of a catalyst in a second reactor to convert these two olefins into HCFC-243fa and HCFC-244fa, respectively; (c) the reaction of HCFC-243fa and HCFC-244fa over a dehydrochlorination catalyst or in a caustic solution in a third reactor to form HCFO-1233zd and HFO-1234ze; and (d) the reaction of HCFO-1233zd(Z) and HFO-1234ze(Z) in the presence of a catalyst in a fourth reactor to form trans-1233zd and trans-1234ze, respectively.

23 Claims, No Drawings

INTEGRATED PROCESS TO CO-PRODUCE 1,1,1,3,3-PENTAFLUOROPROPANE, TRANS-1-CHLORO-3,3,3-TRIFLUOROPROPENE AND TRANS-1,3,3,3-TETRAFLUOROPROPENE

FIELD OF THE INVENTION

A fully integrated process for the co-production of 1,1,1,3,3-pentafluoropropane (HFC-245fa), trans-1-chloro-3,3,3-trifluoropropene (HCFO-1233zd(E)), and trans-1,3,3,3-tetrafluoropropene (HFO-1234ze(E)) is described herein.

BACKGROUND OF THE INVENTION

The use of chlorofluorocarbons or hydrochlorofluorocarbons as foam-blowing agents has been banned due to concerns that their release damages the ozone layer. More recently, foam-blowing (addition of a volatile material to a polymeric mixture to cause a bubbled matrix which imparts insulation or cushioning value) has been accomplished through use of HFC-245fa; however, concern has been raised about the Global Warming Potential of this material.

A leading candidate to eventually replace HFC-245fa in these applications is trans-1-chloro-3,3,3-trifluoropropene, also known as HCFO-1233zd(E). This material also has potential use as a solvent. See for example, U.S. Pat. Nos. 6,844,475, 7,592,494 and 7,829,748. See also, U.S. Patent Publication Nos. 2009-0305876, 2010-0152504 and 2010-0130762. See also, U.S. patent application Ser. No. 12/754,070, filed Apr. 5, 2010. All of the foregoing documents are hereby incorporated herein by reference.

A second candidate for application in single component foam blowing applications is trans-1,3,3,3-tetrafluoropropene, also known as HFO-1234ze(E). See for example U.S. Pat. Nos. 7,230,146 and 7,485,760, which are hereby incorporated herein by reference.

While methods for producing individual compounds have been conducted, it has been a problem in the art to conduct an economical process for the continuous preparation of more than one desired compound, such as the co-production of HCFO-1233zd(E) and HFO-1234ze(E). In addition, since HFC-245fa will continue to be needed for some time as it is slowly phased out and the new products are slowly phased in, this product should also be co-produced.

It has now been found that HCFO-1233zd(E), HFO-1234ze(E) and HFC-245fa may each be continuously and economically co-produced via an integrated manufacturing process which starts with a single chlorinated hydrocarbon, 1,1,1,3,3-pentachloropropane (HCC-240fa), or a derivative thereof, such as 1,1,3,3-tetrachloropropene and 1,3,3,3-tetrachloropropene.

SUMMARY OF THE INVENTION

The present invention is based upon the discovery that HFC-245fa (hereafter 245fa), HFO-1234ze (hereafter 1234ze) and HCFO-1233zd (hereafter 1233zd) can be co-produced from HCC-240fa (hereafter 240fa), or a derivative thereof, such as 1,1,3,3-tetrachloropropene and 1,3,3,3-tetrachloropropene. The product compositions are strongly dependent on the fluorination catalyst used and reaction conditions, and accordingly, the production amount of each of the three products can be conveniently adjusted to fit any market demands.

The disclosed integrated manufacturing process comprises the following main steps:
(a) reacting 240fa (or a derivative thereof, such as 1,1,3,3-tetrachloropropene and 1,3,3,3-tetrachloropropene) with HF in the presence of a catalyst in a liquid phase reactor to form a mixture containing 245fa, 244fa, 1234ze and 1233zd,
(b) after removing HCl and HF, reacting the organic mixture with HCl in the presence of a catalyst in a liquid phase or a gas phase reactor to convert unsaturated olefins into alkanes,
(c) isolating and purifying 245fa product,
(d) dehydrochlorinating 243fa and 244fa in the liquid phase with a caustic solution or in the vapor phase using a dehydrochlorination catalyst to form 1233zd and 1234ze, respectively, and
(e) isolating and purifying trans-1234ze and trans-1233zd products.

One of technical challenges of this invention is the separation between 245fa and trans-1233zd because of their close boiling points. To overcome this difficulty, the unsaturated products, 1233zd and 1234ze, are hydrochlorinated into 243fa and 244fa, respectively, and the 245fa is then isolated from the mixture of 243fa, 244fa, and 245fa. 1233zd and 1234ze can then be produced from the dehydrochlorination of 243fa and 244fa, respectively.

One embodiment of the invention is thus directed to an integrated manufacturing process for co-producing 1,1,1,3,3-pentafluoropropane (245fa), trans-1-chloro-3,3,3-trifluoropropene (1233zd(E)), and trans-1,3,3,3-tetrafluoropropene (1234ze(E)) comprising the steps:
(a) reacting 240fa with HF in the presence of a catalyst to form a mixture containing HCl, HF, an organic mixture of 244fa, 245fa, 1233zd and 1234ze;
(b) removing the HCl and HF from the mixture of step (a) and then reacting the organic mixture with HCl in the presence of a catalyst to convert the unsaturated olefin compounds into a mixture of saturated alkane compounds including 243fa, 244fa and 245fa;
(c) isolating and purifying the 245fa from the mixture of saturated alkane compounds;
(d) dehydrochlorinating the 243fa and 244fa in the mixture of saturated alkane compounds to form 1233zd and 1234ze, respectively, and
(e) isolating and purifying the trans-1234ze and trans-1233zd products generated in step (d).

In certain embodiments, step (a) is conducted in a liquid phase reactor. In certain embodiments, the liquid-phase fluorination reactor is first charged with metal chloride catalyst. In certain embodiments, the metal chloride catalyst is selected from the group comprising $TiCl_4$, $SnCl_4$, $TaCl_5$, $SbCl_3$, $AlCl_3$, $SbCl_5$, and combination thereof. In certain embodiments, the metal chloride catalyst comprises a combination of $SbCl_5$ and $TiCl_4$.

In certain embodiments, step (b) further comprises step (b1) removing trace amounts of unsaturated compounds present after step (b). In certain embodiments, step (b1) is conducted using photochlorination. In certain embodiments, step (b) is conducted in a liquid phase reactor. In certain embodiments, step (b) is conducted in a gas phase reactor.

In certain embodiments, step (d) is conducted in a liquid phase reactor with a caustic solution. In certain embodiments, step (d) is conducted in the vapor phase using a dehydrochlorination catalyst.

Another embodiment of the invention is directed to a process for co-manufacturing 1233zd(E), 1234ze(E), and 245fa which comprises the following steps:
(a) reacting 1,1,1,3,3-pentachloropropane (HCC-240fa) with hydrogen fluoride in the presence of a fluorination catalyst in a first reactor to form a product stream comprising HCl, HF, and an organic mixture of 1233zd, 1234ze, 244fa, and 245fa;

(b) separating and recovering HCl and HF from product stream of step (a);

(c) reacting the organic mixture from step (b) with hydrogen chloride in the presence of a hydrochlorination catalyst in a second reactor to form a product stream comprising 243fa, 244fa, and 245fa;

(d) separating and recovering HCl from product stream of step (c);

(e) optionally removing trace amounts of unsaturated compounds present after step (d) by photo chlorination;

(f) separating and purifying 245fa as a first product;

(g) reacting 243fa and 244fa by dehydrochlorination in a third reactor to form a product stream containing 1233zd and 1234ze;

(h) separating and recovering HCl from the product stream of step (g);

(i) separating and purifying 1234ze(E) and 1233zd(E) as a second product and a third product, from the product stream of step (h);

(j) sending a combined product stream from step (i) which contains 1233zd(Z), 1234ze(Z), 243fa, and 244fa back to the third reactor for a recycle reaction in step (g); and (k) optionally reacting 1233zd(Z) and 1234ze(Z) included in the combined product stream from step (i) in the presence of an isomerization catalyst in a fourth reactor to form a product stream containing 1234ze(E) and 1233zd(E) and separating these compounds from the reaction stream before the recycle step.

In certain embodiments, step (a) is conducted in a liquid phase reactor. In certain embodiments, the liquid-phase fluorination reactor is first charged with metal chloride catalyst. In certain embodiments, the metal chloride catalyst is selected from the group comprising $TiCl_4$, $SnCl_4$, $TaCl_5$, $SbCl_3$, $AlCl_3$, $SbCl_5$, and combination thereof. In certain embodiments, the metal chloride catalyst comprises a combination of $SbCl_5$ and $TiCl_4$.

In certain embodiments, step (g) is conducted in the vapor phase in the presence of a dehydrochlorination catalyst. In certain embodiments, step (g) is conducted in a liquid phase with a caustic solution.

Another embodiment of the invention is directed to a process for co-manufacturing 1233zd(E), 1234ze(E), and 245fa which comprises the following steps:

(a) reacting 1,1,1,3,3-pentachloropropane (240fa) with anhydrous HF in excess in the presence of a catalyst in a liquid-phase reactor to co-produce 1233zd, 1234ze, 244fa, and 245fa, in a first reactor;

(b) reacting 1233zd and 1234ze with HCl in excess in the presence of a catalyst in a second reactor to convert these two olefins into 243fa and 244fa;

(c) dehydrochlorinating 243fa and 244fa in a third reactor to form 1233zd and 1234ze; and (d) reacting 1233zd(Z) and 1234ze(Z) in the presence of a catalyst in a fourth reactor to form trans-1233zd and trans-1234ze, respectively.

DETAILED DESCRIPTION OF THE INVENTION

As described above the present invention is a process whereby trans-1-chloro-3,3,3-trifluoropropene (HCFO-1233zd(E)), trans-1,3,3,3-tetrafluoropropane (HFO-1234ze(E)), and 1,1,1,3,3-pentafluoropropane (HFC-245fa) can be co-produced, in an integrated process, starting with the single hydrochlorocarbon feed material, 1,1,1,3,3-pentachloropropane (HCC-240fa).

This process also avoids intimate contacting of 1233zd(E) and 245fa which form an azeotropic composition that makes it difficult to separate using conventional separation techniques such as distillation.

This process also has an advantage in that it allows for great flexibility in producing different amounts of each of the three desired compounds, simply by adjusting the operating conditions or concentrations of reactants and/or catalyst in the first liquid phase reactor.

Overall Chemistry

The chemistry of this invention involves the following reactions:

(a) the reaction of 1,1,1,3,3-pentachloropropane (240fa), or a derivative thereof, such as 1,1,3,3-tetrachloropropene and 1,3,3,3-tetrachloropropene, with anhydrous HF in excess in the presence of a catalyst in a liquid-phase reactor in such a way as to co-produce 1-chloro-3,3,3-trifluoropropene (1233zd), 1,3,3,3-tetrafluoro-propene (1234ze), 3-chloro-1,1,1,3-tetrafluoropropane (244fa), and 1,1,1,3,3-pentafluoropropane (245fa) in a first reactor;

(b) the reaction of 1233zd and 1234ze with HCl in excess in the presence of a catalyst in a second reactor to convert these two olefins into 243fa and 244fa, respectively;

(c) the reaction, by dehydrochlorination, of 243fa and 244fa, either over a dehydrochlorination catalyst or in a caustic solution, in a third reactor to form 1233zd and 1234ze; and (d) the reaction of 1233zd(Z) and 1234ze(Z) in the presence of a catalyst in a fourth reactor to form trans-1233zd and trans-1234ze, respectively.

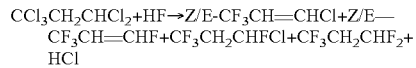  Reaction 1

  Reaction 2

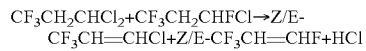  Reaction 3

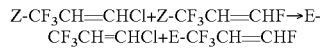  Reaction 4

In a preferred embodiment, Reactions 3 and 4 can be combined and carried out in a single gas-phase reactor charged with a single catalyst that can catalyze both the dehydrochlorination of 243fa and 244fa and the isomerization of 1233zd (Z) and 1234ze(Z).

One embodiment of the invention provides a process for co-manufacturing 1233zd(E), 1234ze(E), and 245fa which comprises the following steps:

(a) reacting 240fa with HF in the presence of a catalyst to form a mixture containing HCl, HF, an organic mixture of 244fa, 245fa, 1233zd and 1234ze;

(b) removing the HCl and HF from the mixture of step (a) and then reacting the organic mixture with HCl in the presence of a catalyst to convert the unsaturated olefin compounds into a mixture of saturated alkane compounds including 243fa, 244fa and 245fa;

(c) isolating and purifying the 245fa from the mixture of saturated alkane compounds;

(d) dehydrochlorinating the 243fa and 244fa in the mixture of saturated alkane compounds to form 1233zd(Z/E) and 1234ze(Z/E), respectively, and (e) isolating and purifying the trans-1234ze and trans-1233zd products generated in step (d).

In certain embodiments, step (b) further comprises step (b1), removing trace amounts of unsaturated compounds present after step (b). Advantageously, step (b1) is conducted using photochlorination.

In certain embodiments, step (a) is conducted in a liquid phase reactor. In certain embodiments, step (b) is conducted in a liquid phase reactor. In certain embodiments, step (b) is conducted in a gas phase reactor.

In certain embodiments, step (d) is conducted in a liquid phase reactor with a caustic solution. In certain embodiments, step (d) is conducted in the vapor phase using a dehydrochlorination catalyst.

Another embodiment of the invention is directed to a process for co-manufacturing 1233zd(E), 1234ze(E), and 245fa which comprises the following steps:

(a) reacting 1,1,1,3,3-pentachloropropane (HCC-240fa) with hydrogen fluoride in the presence of a fluorination catalyst in a first reactor to form a product stream comprising HCl, HF, and an organic mixture of 1233zd, 1234ze, 244fa, and 245fa;

(b) separating and recovering HCl and HF from product stream of step (a);

(c) reacting the organic mixture from step (b) with hydrogen chloride in the presence of a hydrochlorination catalyst in a second reactor to form a product stream comprising 243fa, 244fa, and 245fa;

(d) separating and recovering HCl from product stream of step (c);

(e) optionally removing trace amounts of unsaturated compounds present after step (d) by photo chlorination;

(f) separating and purifying 245fa as a first product;

(g) reacting 243fa and 244fa by dehydrochlorination in a third reactor to form a product stream containing cis/trans-1233zd and cis/trans-1234ze;

(h) separating and recovering HCl from the product stream of step (g);

(i) separating and purifying 1234ze(E) and 1233zd(E) as a second product and a third product, from the product stream of step (h);

(j) sending a combined product stream from step (i) which contains 1233zd(Z), 1234ze(Z), 243fa, and 244fa back to the third reactor for a recycle reaction in step (g); and (k) optionally reacting 1233zd(Z) and 1234ze(Z) included in the combined product stream from step (i) in the presence of an isomerization catalyst in a fourth reactor to form a product stream containing 1234ze(E) and 1233zd(E) and separating these compounds from the reaction stream before the recycle step.

In certain embodiments, step (g) takes place in the presence of a dehydrochlorination catalyst. In certain embodiments, step (g) takes place in caustic solution.

Yet another embodiment of the invention is directed to a process for co-manufacturing 1233zd(E), 1234ze(E), and 245fa which comprises the following steps:

(a) reacting 240fa with anhydrous HF in excess in the presence of a catalyst in a liquid-phase reactor to co-produce 1233zd, 1234ze, 244fa, and 245fa in a first reactor;

(b) reacting 1233zd and 1234ze with excess HCl in the presence of a catalyst in a second reactor to convert these two olefins into 243fa and 244fa, respectively;

(c) reacting the 243fa and 244fa over a dehydrochlorination catalyst or in a caustic solution in a third reactor to form 1233zd(E/Z) and 1234ze(E/Z); and (d) reacting 1233zd(Z) and 1234ze(Z) from step (c) in the presence of a catalyst in a fourth reactor to form trans-1233zd and trans-1234ze, respectively.

1. HCC-240fa Fluorination

Liquid-phase fluorination reactor is first charged with metal chloride catalyst selected from the group comprising $TiCl_4$, $SnCl_4$, $TaCl_5$, $SbCl_3$, $AlCl_3$, $SbCl_5$, and their various combinations. A combination of $SbCl_5$ and $TiCl_4$ is most preferred. HF is first added in an amount to totally fluorinate the metal chloride catalyst. The catalyst fluorination is conducted while the reactor is at 10° C. to 50° C. and at about 0 to 160 psig pressure. HCl generated during catalyst fluorination can be vented out of the top of the catalyst stripper column in order to control the reactor pressure at or below the intended operating pressure of the reactor. Preferably the reactor is constructed from materials which are resistant to the corrosive effects of the HF and catalyst, such as Hastelloy-C, Inconel, Monel, Incoloy, or fluoropolymer-lined steel vessels.

Once catalyst fluorination is completed, an additional amount of HF is added to the reactor to fill the reactor to 20% to 90% of its volume while the reactor is heated to a temperature of 85° C. to 95° C. and agitated. Then the addition of the HCC-240fa can be started immediately to cause continuous reaction while maintaining the flow of HF at an amount sufficient to produce the desired products. The reaction runs under HF rich conditions to produce the reaction co-products, 1233zd, 1234ze, 244fa and 245fa, with desired ratios.

General operating conditions are: operating pressure of 80 to 140 psig maintained by a control valve on the exiting flow from the stripper column; reactor temperature of 85° C. to 115° C., primarily supplied by steam flow into the reactor jacket; application of brine cooling to the heat exchanger on top of the stripper column to induce reflux; temperature in the center portion of the stripper about 10° C. to 40° C. below that in the reactor; additional heat input by superheating the HF vapor feed with high-pressure steam to 120° C. to 150° C.; feed rate of HF to maintain reactor and stripper conditions.

The stream exiting the stripper column enters a recycle column. Here the high boiling underfluorinated intermediates and some HF are separated and returned to fluorination reactor for further reaction. The stream exiting the recycle column and containing 1233zd, 1234ze, 244fa, 245fa, HF, and HCl is fed to HCl recovery column. The HCl in this stream can then be purified and collected using a low-temperature HCl distillation column. High purity HCl is isolated and sent to a down-stream hydrochlorination reactor.

The bottom stream from the HCl column that contains a crude product mixture of 1233zd, 1234ze, 244fa, 245fa, and HF is fed to a sulfuric extractor or a phase separator for removal of HF from this mixture. HF is either dissolved in the sulfuric acid or phase separated from the organic mixture. HF is desorbed from the sulfuric acid/HF mixture by stripping distillation and recycled back to the up-stream fluorination reactor. The organic mixture from the overhead of the sulfuric acid extractor may require further treatment (scrubbing or adsorption) to remove trace amount of HF before it is fed to a down-stream hydrochlorination reactor.

2. HCFO-1233zd and HFO-1234ze Hydrochlorination

The HF and HCl-free organic product stream which mainly contains 1233zd, 1234ze, 244fa, and 245fa is then fed into a hydrochlorination reactor to convert 1233zd and 1234ze into 243fa and 244fa, respectively. The hydrochlorination reaction can be carried out using either a liquid or a solid catalyst. The liquid phase system operates at about 80° C. to 150° C. The solid catalyst reactor system operates at about 300° C. to 350° C. for complete reaction. The liquid phase system generally is carried out by bubbling mixed HCl and organic feed through a pot containing the liquid catalyst.

Catalysts for the liquid phase reaction are solutions of metal chlorides such as aluminum chloride, ferric chloride, tin chloride, gallium chloride, cobalt chloride, nickel chloride, zinc chloride, and their various combinations. The solvent capable of dissolving the catalyst can be water or an organic compound. The reaction is carried out by contacting the reacting gases with the solution of the metal chlorides. The composition of the liquid catalyst is so adjusted that the temperature of the solution can readily be held at desired value. The temperature must be sufficiently high to prevent condensation of solvent of reaction in the reactor; at the same time, it must not be so high that the reacting gases will sweep out catalyst solution solvent from the reactor. The reaction runs under HCl rich conditions for complete conversion of unsaturates.

The solid catalyst system generally is operated by co-feeding mixed HCl and organic feed through a fix-bed reactor containing a solid catalyst. Catalysts used include metal chlorides such as aluminum chloride, ferric chloride, tin chloride, gallium chloride, cobalt chloride, nickel chloride, zinc chloride, thorium oxychloride, rare-earth oxides, and their various combinations. The metal chlorides, oxychlorides, and oxides usually are deposited on a carrier such as carbon, silica gel, and alumina. The reaction runs under HCl rich conditions for complete conversion of unsaturates.

The stream exiting the hydrochlorination reactor is fed to HCl recovery column. The HCl in this stream can then be purified and collected using a low-temperature HCl distillation column. High purity HCl is isolated and sent back to the up-stream hydrochlorination reactor for recycle.

Optionally, the stream exiting HCl recovery column is fed into a photo-chlorination reactor, in which chlorine ($Cl_2$) reacts with the unsaturated (olefinic) impurities to form the corresponding saturated halogenated hydrocarbons in the presence of an ultraviolet light source. 1233zd and 1234ze impurities will be converted into 2,3,3-trichloro-1,1,1-trifluoropropane and 2,3-dichloro-1,1,1,3-tetrafluoropropane, respectively, in the photochlorination reactor.

In a useful photochlorination process, light from a suitable source is directed through a reactor wall to interact with the reactants therein. The source of light may be any one of a number of arc or filament lamps known in the prior arts. Quartz or borosilicate glass such as Pyrex glass may be employed as transparent material to construct the portion of the reactor wall through which the light passes and enters the reactor. The photochlorination may be continuously carried out in the gas phase, in which starting materials are vaporized and contacted with chlorine vapor in a reaction zone. Suitable reaction temperatures may be ranged from room temperature to about 50° C.

Alternatively the photochlorination may be carried out in the liquid phase by feeding chlorine to a reactor containing starting materials. It is a convenient practice to control the reaction temperature below the boiling points of the starting materials and products.

The HCl-free organic stream mainly containing 243fa, 244fa and 245fa is fed forward for the purification of the first product, namely, 245fa, in the integrated process.

3. Purification of HFC-245fa

Purification of final product 245fa consists of two continuously operating distillation columns. The first ($1^{st}$) column is used to remove any light ends from the 245fa crude and the second ($2^{nd}$) column is used to remove the heavier components, primarily 243fa and 244fa. Product grade 245fa is isolated in the $2^{nd}$ column overhead. The remaining mixture of 243fa and 244fa, recovered from the $2^{nd}$ column bottom, is sent to a down-stream dehydrochlorination reactor.

The distillation may be preferably conducted in a standard distillation column at atmospheric pressure, super-atmospheric pressure or a vacuum. Preferably the pressure is less than about 300 psig, more preferably less than about 150 psig and most preferably less than 100 psig. The pressure of the distillation column inherently determines the distillation operating temperature. 245fa, 244fa, and 243fa have boiling points of about 15° C., about 42° C., and from about 71° C. to 74° C., respectively. 245fa may be recovered as distillate by operating the distillation column at from about 30° C. to about 100° C. Single or multiple distillation columns may be used.

4. HCFC-243fa and HCFC-244fa Dehydrochlorination

In the dehydrochlorination reactor, 243fa and 244fa are converted into 1233zd and 1234ze, respectively. Preferably dehydrochlorination of 243fa and 244fa is carried out in a vapor phase, and more preferably in a fixed-bed reactor in the vapor phase. The dehydrochlorination reaction may be conducted in any suitable reaction vessel or reactor, but it should preferably be constructed from materials which are resistant to the corrosive effects of hydrogen chloride such as nickel and its alloys, including Hastelloy, Inconel, Incoloy, and Monel or vessels lined with fluoropolymers. These may be single pipe or multiple tubes packed with a dehydrochlorinating catalyst which may be one or more of halogenated metal oxides in bulk form or supported, metal halides in bulk form or supported, and carbon supported transition metals. Suitable catalysts non-exclusively include fluorinated chromia, chromium fluoride, fluorinated alumina, aluminum fluoride, alumina chloride, ferric chloride, fluorinated magnesia, magnesium fluoride, alkali metal halide (LiCl, LiF, KCl, KF, CsCl, CsF, etc.) doped fluorinated magnesia, alkali metal halide alkali metal halide (LiCl, LiF, KCl, KF, CsCl, CsF, etc.) doped magnesium fluoride, carbon supported alkali metal halide (LiCl, LiF, KCl, KF, CsCl, CsF, etc.), di-valent metal halide ($MgCl_2$, $MgF_2$, $NiCl_2$, $CuCl_2$, etc), and metal (iron, cobalt, nickel, and palladium etc.), and bulk metal alloys such as Monel 400, Inconel 625, etc. The mixture of 243fa and 244fa is introduced into the reactor either in pure form, impure form, or together with an optional inert gas diluent such as nitrogen, argon, or the like.

In a preferred embodiment of the invention, the mixture of 243fa and 244fa is pre-vaporized or preheated prior to entering the reactor. Alternatively, the mixture of 243fa and 244fa is vaporized inside the reactor. Useful reaction temperatures may range from about 200° C. to about 600° C. Preferred temperatures may range from about 250° C. to about 450° C., and more preferred temperatures may range from about 300° C. to about 350° C. The reaction may be conducted at atmospheric pressure, super-atmospheric pressure or under vacuum. The vacuum pressure can be from about 5 Torr to about 760 Torr. Contact time of the organic feed with the catalyst may range from about 0.5 seconds to about 120 seconds, however, longer or shorter times can be used.

In the preferred embodiment, the process flow is in the down or up direction through a bed of the catalyst. It may also be advantageous to periodically regenerate the catalyst after prolonged use while in place in the reactor. Regeneration of the catalyst may be accomplished by any means known in the art, for example, by passing air or air diluted with nitrogen over the catalyst at temperatures of from about 200° C. to about 500° C., preferably from about 300° C. to about 400° C., for from about 0.5 hour to about 3 days. This is followed by $H_2$ treatment at temperatures of from about 100° C. to about 400° C., preferably from about 200° C. to about 300° C. for supported transition metal catalysts.

The stream exiting the gas-phase dehydrochlorination reactor is fed to HCl recovery column. The HCl in this stream can then be purified and collected using a low-temperature HCl distillation column. High purity HCl is isolated and sent back to the up-stream hydrochlorination reactor for recycle. Optionally, HCl is scrubbed using a water or caustic absorption unit followed by a drying column.

Alternative Embodiment

In an alternative embodiment of the invention, dehydrochlorination of 243fa and 244fa can also be accomplished by reacting the mixed feed with a strong caustic solution that includes, but is not limited to KOH, NaOH, $Ca(OH)_2$ and CaO at an elevated temperature. The caustic solution is essentially a liquid (whether a solution, dispersion, emulsion, or suspension and the like). In some embodiments, the caustic strength of the caustic solution is from about 2 wt. % to about 100 wt. %, more preferably from about 5 wt. % to about 90 wt. % and most preferably from about 10 wt. % to about 80 wt. %. The reaction may be conducted at a temperature of from about 20° C. to about 100° C., more preferably from about 40° C. to about 90° C. and most preferably from about 50° C. to about 70° C. As above, the reaction may be conducted at atmospheric pressure, super-atmospheric pressure or under vacuum. The vacuum pressure can be from about 5 Torr to about 760 Torr. In addition, a solvent may optionally be used to help dissolve the organic compounds in the caustic solution. This optional step may be conducted using solvents that are well known in the art for said purpose. The product stream is dried in a drying column.

The HCl-free organic stream mainly containing 1233zd, 1234ze, 243fa, and 244fa is fed forward for the purification of the second and third products, namely, 1233zd(E) and 1234ze (E), in the integrated process.

5. Purification of HFO-1234ze(E) and HCFO-1233zd(E)

Purification of final products 1233zd(E) and 1234ze(E) consists of four continuously operating distillation columns. The first column is used to remove light components from the crude. The heavy ends from the first column are fed to a second column in which 1234ze(E) is isolated in the column overhead. The third column takes the heavy ends from the second column and separates 1234ze(Z) as an overhead product. The third column bottoms mainly contain 1233zd(E), 1233zd(Z), 2443fa and 244fa. The fourth column takes the heavy ends from the third column and produces product grade 1233zd(E) as an overhead product. The fourth column bottom stream mainly containing 1233zd(Z), 243fa, and 244fa is combined with the third column overhead stream mainly containing 1234ze(Z). The combined stream is sent to a down-stream isomerization reactor before recycle or the up-stream dehydrochlorination reactor for direct recycle in a preferred embodiment. It should be recognized that at some point a purge of heavy byproducts from this stream will also be required.

The distillation may be preferably conducted in a standard distillation column at atmospheric pressure, super-atmospheric pressure or a vacuum. Preferably the pressure is less than about 300 psig, more preferably less than about 150 psig and most preferably less than 100 psig. The pressure of a distillation column inherently determines the distillation operating temperature. 1234ze(E), 1234ze(Z), 1233zd(E), 1233zd(Z), 244fa and 243fa have boiling points of −19° C., 9° C., 19° C., 38° C., about 42° C., and from about 71° C. to 74° C., respectively. 1234ze(E) and 1233zd(E) may be recovered as distillate by operating the distillation column at from about 30° C. to about 100° C. Single or multiple distillation columns may be used.

6. HCFO-1233zd(Z) and HCFO-1234ze(Z) Isomerization

1234ze(Z) and 1233zd(Z) included in the mixture of 1234ze(Z), 1233zd(Z), 243fa, and 244fa can be isomerized into their trans-isomers in an isomerization reactor. The isomerization reaction may be conducted in any suitable reaction vessel or reactor, but it should preferably be constructed from materials which are resistant to corrosion such as nickel and its alloys, including Hastelloy, Inconel, Incoloy, and Monel. These may be single pipe or multiple tubes packed with an isomerization catalyst which may be a halogenated metal oxide, a metal halide, or a carbon supported transition metal. Suitable catalysts non-exclusively include fluorinated chromia, chromium fluoride, fluorinated alumina, aluminum fluoride, alumina chloride, ferric chloride, fluorinated magnesia, magnesium fluoride, alkali metal halide (LiCl, LiF, KCl, KF, CsCl, CsF, etc.) doped fluorinated magnesia, alkali metal halide alkali metal halide (LiCl, LiF, KCl, KF, CsCl, CsF, etc.) doped magnesium fluoride, and carbon supported iron, cobalt, nickel, or palladium.

Useful isomerization reaction temperatures may range from about 25° C. to about 450° C. Preferred temperatures may range from about 50° C. to about 350° C., and more preferred temperatures may range from about 100° C. to about 250° C. The reaction may be conducted at atmospheric pressure, super-atmospheric pressure or under vacuum. The vacuum pressure can be from about 5 Torr to about 760 Torr. Contact time of the cis-1,3,3,3-tetrafluoropropene with the catalyst may range from about 0.5 seconds to about 120 seconds, however, longer or shorter times can be used.

Applicants have found that when the same catalyst is used for dehydrochlorination and for isomerization, the reactions of 243fa and 244fa dehydrochlorination and 1234ze(Z) and 1233zd(Z) isomerization can be combined and carried out in the same reactor. Thus, in a preferred embodiment, the mixture of 1234ze(Z), 1233zd(Z), 243fa, and 244fa is directly sent back to the up-stream dehydrochlorination reactor for direct recycle.

The following examples are provided to further illustrate the invention and should not be taken as limitations of the invention.

EXAMPLE 1

240fa Fluorination in the Presence of a Titanium Chloride Catalyst

A clean, empty ten gallon jacketed, agitated reactor of Hastelloy C construction was prepared. This reactor was connected to a two inch inner diameter vertical, PTFE-lined pipe containing packing material (stripper), which was in turn connected to an overhead heat exchanger. The heat exchanger was supplied with −40° C. brine circulation on the shell side. Vapors exiting this stripper were processed through a scrubber, in which temperature-controlled dilute potassium hydroxide aqueous solution was circulated. Vapors exiting this stripper were collected in a weighed, chilled (−40° C.) cylinder referred to as the product collection cylinder, followed by a smaller cylinder in series chilled in a dry ice bath.

14 lbs. of anhydrous HF was fed to assure catalyst fluorination. Next, 1.5 lbs. of $TiCl_4$ was added as a catalyst. HCl was immediately generated as observed by the build-up of pressure in the reactor. After the pressure was reduced by venting most of the HCl from the system, 50 lbs. of 240fa was added. The reactor was heated. At about 85° C. HCl started to be generated indicating that the fluorination reaction was initiated. The system pressure was controlled at about 120 psig. Additional HF was then fed continuously and product was collected in the product collection cylinder until the 240fa was consumed.

The GC analysis of the crude material collected during the run was as follows; 86.4% 1233zd(E); 5.5% G-244fa; 3.1% 1234ze(E); 1.5% 1233zd(Z); 1.1% 1234ze(Z); 1.1% dimer; 0.2% trifluoropropyne.

EXAMPLE 2

240fa Fluorination in the Presence of Antimony Pentachloride Catalyst

A 600-mL Monel autoclave equipped with mechanical stirrer was charged with 8.7 g $SbCl_5$ and cooled to $-27°$ C. The autoclave was then evacuated and charged with 49.8 g of anhydrous HF. The contents were cooled to $-40°$ C., and 44 g HCC-240fa was added. The reactor was then connected to a packed column/condenser assembly. The condenser was maintained at $-20°$ C. The reaction mixture was heated to 135° C. over 2.25 hours and maintained at that temperature for an additional 2 hours. During this heating period, the pressure in the autoclave was maintained from about 1965 to 2655 KPa (300-400 psig) by periodically venting pressure (HCl by-product) in excess of 2655 KPa (400 psig). Venting was done from the top of the condenser to a cold aqueous KOH scrubber which was connected to $-78°$ C. cold trap. The reactor was then completely vented to the cold trap. 18.5 g of a colorless liquid were collected. The identity of this liquid was determined by GC analysis to be 84% HCF-245fa (corresponding to a yield of 57%) and 11% HCFC-244fa.

EXAMPLE 3

HFO-1234ze and HCFO-1233zd Hydrochlorination in the Presence of an $AlCl_3/Al_2O_3$ Catalyst A 10 wt % $AlCl_3/Al_2O_3$ catalyst is used for the hydrochlorination of 1234ze and 1233zd. A cylindrical Monel reactor of ¾ inch diameter immersed into a 3-zone electrical furnace is used. Process temperatures are recorded using a multi-point thermocouple placed inside the reactor and within the catalyst bed. The distance between two adjacent probe points is 4 inches. The catalyst is loaded in such a way that its bed is within two adjacent probe points. Organic is fed into the bottom of the vertically mounted reactor and was vaporized before reaching catalyst bed. Effluent gases are passed through a gas sampling tube and the progress of the reaction is monitored periodically via GC analysis of the contents of the gas sampling tube. 20 ml of catalyst is charged into the Monel reactor. Reactor is heated to 350° C. in $N_2$ flow (100 ml/min). Once reactor temperatures are stabilized, $N_2$ flow is stopped and HCl flow (150 ml/min) is started. An organic feed containing about 50.0 wt % 1233zd(E) and 50.0 wt % 1234ze (E) is then introduced into the reactor at the rate of 12 g/hr. GC analysis conducted after 1 h on stream indicates the effluent contains 0.2% of 1234ze(E), 0.3% of 1233zd(E), 47.0% of 244fa, and 52.0% 243fa.

EXAMPLE 4

HCFC-243fa Dehydrochlorination in the Presence of Tri-Valent Halogenated Metal Oxide/Tri-Valent Metal Halide Catalysts Tri-valent halogenated metal oxide and tri-valent metal halides are used for 243fa dehydrochlorination. A cylindrical Monel reactor of ¾ inch diameter immersed into a 3-zone electrical furnace is used. Process temperatures are recorded using a multi-point thermocouple placed inside the reactor and within the catalyst bed. The distance between two adjacent probe points is 4 inches. The catalyst is loaded in such a way that its bed is within two adjacent probe points. Organic is fed into the bottom of the vertically mounted reactor and was vaporized before reaching catalyst bed. Effluent gases are passed through a gas sampling tube and the progress of the reaction is monitored periodically via GC analysis of the contents of the gas sampling tube. In each case, 20 ml of catalyst is charged into the Monel reactor. A 99.9% 243fa feed is flowed over catalyst at a rate of 12 g/h. As shown in Table 1, all the catalysts listed in Table 1 exhibit a high activity (>70% 243fa conversion) and a high selectivity to 1233zd(E+Z) (>95%) during 243fa dehydrochlorination.

TABLE 1

243fa dehydrochlorination over various catalysts

| Catalyst | Temp., °C. | HCFC-243fa conv., % | Selectivity, % | | |
|---|---|---|---|---|---|
| | | | 1233zd(E) | 1233zd(Z) | others |
| Fluorinated $Cr_2O_3$ | 250 | 91.0 | 90.6 | 8.5 | 0.9 |
| $AlF_3$ | 300 | 90.0 | 88.1 | 10.8 | 1.1 |
| 10 wt % $FeCl_3$/Carbon | 325 | 85.0 | 85.2 | 13.3 | 1.5 |

Reaction Conditions: 20 ml catalyst, 12 g/h 243fa, 1 atm

EXAMPLE 5

HCFC-244fa Dehydrohalogenation in the Presence of Tri-Valent Halogenated Metal Oxide/Tri-Valent Metal Halide Catalysts Fluorinated $Cr_2O_3$ and $AlF_3$ were used as dehydrohalogenation catalysts. A cylindrical Monel reactor of ¾ inch diameter immersed into a 3-zone electrical furnace was used. Process temperatures were recorded using a multi-point thermocouple placed inside the reactor and within the catalyst bed. The distance between two adjacent probe points was 4 inches. The catalyst was loaded in such a way that its bed was within two adjacent probe points. Organic was fed into the bottom of the vertically mounted reactor and was vaporized before reaching catalyst bed. Effluent gases were passed through a gas sampling tube and the progress of the reaction was monitored periodically via GC analysis of the contents of the gas sampling tube. 20 ml of catalyst was charged into the reactor. 244fa feed was passed through the catalyst at a rate of 12 g/hour at a temperature of 350° C.

As shown in Table 2, the fluorinated $Cr_2O_3$ catalyst provided a 1233zd(E+Z) selectivity of about 75% and a 1234ze (E+Z) selectivity of about 21%, demonstrating that 1234ze (E+Z) and 1233zd(E+Z) can be co-produced from 244fa dehydrohalogenation over this catalyst. All 244fa was converted during the reaction.

TABLE 2

244fa dehydrohalogenation over a fluorinated metal oxide catalyst at 350° C.

| Catalyst | HCFC-244fa conv. (%) | Selectivity (%) | | | |
|---|---|---|---|---|---|
| | | 1234ze (E + Z) | 245fa | 1233zd (E + Z) | others |
| Fluorinated $Cr_2O_3$ | 100.0 | 20.7 | 0.0 | 74.6 | 4.7 |
| $AlF_3$ | 100.0 | 21.8 | 0.0 | 77.3 | 0.9 |

EXAMPLE 6

HCFC-244fa Dehydrohalogenation in the Presence of Supported Mono- and Bi-Valent Metal Halide Catalysts A series of carbon supported mono- and bi-valent metal chlorides were used as dehydrohalogenation catalysts. A cylindrical Monel reactor of ¾ inch diameter immersed into a 3-zone electrical furnace was used. Process temperatures were recorded using a multi-point thermocouple placed inside the reactor and within the catalyst bed. The distance between two adjacent probe points was 4 inches. The catalyst was loaded in such a way that its bed was within two adjacent probe points. Organic was fed into the bottom of the vertically mounted reactor and was vaporized before reaching catalyst bed. Effluent gases were passed through a gas sampling tube and the progress of the reaction was monitored periodically via GC analysis of the contents of the gas sampling tube. 20 ml of catalyst was charged into the Monel reactor. 244fa was passed over each catalyst at a rate of 12 g/h at a temperature of 350° C.

As shown in Table 3, all the mono- and bi-valent metal chloride catalysts provided a 1234ze(E+Z) selectivity higher than 80% and a 1233zd(E+Z) selectivity lower than 20%, indicating these catalysts are more active for 244fa dehydrochlorination than its dehydrofluorination. In comparison, the mono-valent metal chloride catalysts are more selective to form 1234ze(E+Z) than bi-valent metal chloride ones. 244fa conversion higher than 90% was achieved over the following catalysts: 10.0 wt % LiCl/C, 10.0 wt % KCl/C, and 10.0 wt % MgCl$_2$/C.

TABLE 3

244fa dehydrohalogenation over metal chloride catalysts at 350° C.

| Catalyst | Conversion, % 244fa | Selectivity, % 1234ze (E + Z) | 245fa | 1233zd (E + Z) | others |
|---|---|---|---|---|---|
| 10.0 wt % LiCl/C | 96.2 | 95.2 | 0.0 | 4.4 | 0.4 |
| 10.0 wt % KCl/C | 97.9 | 94.4 | 0.0 | 4.9 | 0.7 |
| 10.0 wt % MgCl$_2$/C | 99.3 | 92.9 | 0.0 | 6.7 | 0.4 |
| 10.0 wt % NiCl$_2$/C | 89.3 | 93.4 | 0.0 | 5.4 | 1.2 |
| 10.0 wt % CuCl$_2$/C | 28.5 | 83.8 | 0.0 | 13.0 | 3.2 |

EXAMPLE 7

Isomerization of HCFO-1233zd(Z)

Conversion of 1233zd(Z) into 1233zd(E) was performed using a Monel™ reactor (ID 2 inch, length 32 inch) equipped with a Monel™ preheater (ID 1 inch, length 32 inch) which was filled with Nickel mesh to enhance heat transfer. The reactor was filled with 1.5 L of pelletized fluorinated Cr$_2$O$_3$ catalyst. Nickel mesh was placed at the top and at the bottom of reactor to support the catalyst. A multi-point thermocouple was inserted at the center of the reactor. A feed containing about 10.0 wt % 1233zd(E) and 86.3 wt % 1233zd(Z) was introduced into the reactor at the rate of 0.7 lb/hr. The feed was vaporized prior to entering the reactor preheater. The reactor temperature for this experiment was varied between 100° C. and 200° C. The temperature gradient throughout the reactor never exceeded from 3° C. to 5° C. Samples of reaction products were taken every hour and GC analysis of those samples is given in Table 4.

TABLE 4

| Reaction Temperature ° C. | Area Percent by GC 1233zd(E) | 1233zd(Z) | Others |
|---|---|---|---|
| Initial | 10.0 | 86.3 | 3.7 |
| 103 | 69.6 | 27.9 | 2.5 |
| 104 | 69.8 | 27.9 | 2.4 |
| 128 | 70.2 | 27.6 | 2.2 |
| 128 | 65.0 | 32.8 | 2.2 |
| 128 | 62.8 | 35.0 | 2.2 |
| 128 | 60.9 | 36.9 | 2.2 |
| 151 | 60.8 | 37.1 | 2.1 |
| 151 | 61.8 | 36.2 | 2.0 |
| 151 | 62.4 | 35.6 | 2.0 |
| 151 | 58.9 | 39.0 | 2.1 |
| 181 | 62.2 | 35.8 | 2.0 |
| 199 | 68.3 | 29.4 | 2.3 |

EXAMPLE 8

Isomerization of HFO-1234ze(Z)

Three different kinds of catalysts, namely, fluorinated metal oxide, metal fluoride(s), and supported metal, were used for cis-1234ze isomerization in Example 7. A cylindrical Monel reactor of ¾ inch diameter immersed into a 3-zone electrical furnace was used. Process temperatures were recorded using a multi-point thermocouple placed inside the reactor and within the catalyst bed. The distance between two adjacent probe points was 4 inches. The catalyst was loaded in such a way that its bed was within two adjacent probe points. Organic was fed into the bottom of the vertically mounted reactor and was vaporized before reaching catalyst bed. Effluent gases were passed through a gas sampling tube and the progress of the reaction was monitored periodically via GC analysis of the contents of the gas sampling tube.

In each case, 20 cc of catalyst was used. A mixture of 85.3% 1234ze(Z) and 14.7% 245fa was flowed over catalyst at a rate of 12 g/h. For a specified catalyst, a suitable reaction temperature was carefully chosen such that almost no dehydro-fluorination reaction occurs to the 245fa included in the feed. As shown in Table 5, all the catalysts except 0.5 wt % Co/AC listed in Table 5 provided a high activity (>80% 1234ze(Z) conversion) and a high selectivity to 1234ze(E) (>95%) during 1234ze(Z) isomerization. The 0.5 wt % Co/AC catalyst exhibited a moderate activity (45% of 1234ze (Z) conversion) and a high selectivity 1234ze(E) (about 98%).

TABLE 5

Isomerization of HFO-1234ze(Z) over various catalysts

| Catalyst | reaction temp. (° C.) | conversion, % 1234ze(Z) | selectivity, % 1234ze(E) |
|---|---|---|---|
| Fluorinated Cr$_2$O$_3$ | 100 | 91.0 | 100.0 |
| AlF$_3$ | 200 | 85.2 | 99.3 |
| 0.5 wt % Co/AC | 350 | 45.0 | 98.2 |

Reaction Conditions: 20 cc catalyst, 12 g/h 85.3% 1234ze(Z)/14.7% 245fa, 1 atm

EXAMPLE 9

HF Recovery

This example illustrates the recovery of anhydrous HF from a mixture of HF, 1233zd(E), and 244fa according to certain preferred embodiments of the present invention.

A mixture consisting of about 30 wt. % 1233zd(E), 40 wt. % 244fa, and about 30 wt. % HF is vaporized and fed to the bottom of a packed column at a feed rate of about 2.9 lbs per hour for about 4 hours. A stream of about 80wt. % sulfuric acid (80/20 $H_2SO_4/H_2O$) with about 2% HF dissolved therein is fed continuously to the top of the same packed column at a feed rate of about 5.6 lbs per hour during the same time frame. A gaseous stream exiting the top of the column comprises 1233zd(E) and 244fa with less than 1.0 wt. % HF therein. The concentration of HF in the sulfuric acid in the column bottoms increases from 2.0 wt. % to about 15 wt. %.

The column bottoms containing sulfuric acid and about 15 wt. % HF is collected and charged into a 2 gallon Teflon-lined vessel. The mixture is heated to about 140° C. to vaporize and flash off HF product, which is collected. The collected HF product contains about 6000 ppm water and 500 ppm sulfur. The sulfuric acid contains about 500 ppm of TOC (total organic carbon).

The HF collected from flash distillation is distilled in a distillation column and anhydrous HF is recovered. The recovered anhydrous HF contains less than 50 ppm of sulfur impurities and lees than 100 ppm water.

While the present invention has been particularly shown and described with reference to preferred embodiments, it will be readily appreciated by those of ordinary skill in the art that various changes and modifications may be made without departing from the scope of the invention. It is intended that the claims be interpreted to cover the disclosed embodiment, those alternatives which have been discussed above and all equivalents thereto.

What is claimed is:

1. An integrated manufacturing process for co-producing 1,1,1,3,3-pentafluoropropane (245fa), trans-1-chloro-3,3,3-trifluoropropene (1233zd(E)), and trans-1,3,3,3-tetrafluoropropene (1234ze(E)) comprising the steps:
   (a) reacting 240fa, or a derivative thereof selected from 1,1,3,3-tetrachloropropene and 1,3,3,3-tetrachloropropene, with HF in the presence of a catalyst to form a mixture containing HCl, HF, an organic mixture of 244fa, 245fa, 1233zd and 1234ze;
   (b) removing the HCl and HF from the mixture of step (a) and then reacting the organic mixture with HCl in the presence of a catalyst to convert the unsaturated olefin compounds into a mixture of saturated alkane compounds including 243fa, 244fa and 245fa;
   (c) isolating and purifying the 245fa from the mixture of saturated alkane compounds;
   (d) dehydrochlorinating the 243fa and 244fa in the mixture of saturated alkane compounds to form 1233zd and 1234ze, respectively, and
   (e) isolating and purifying the trans-1234ze and trans-1233zd products generated in step (d).

2. The process of claim 1, wherein step (a) is conducted in a liquid phase reactor.

3. The process of claim 2, wherein the liquid-phase fluorination reactor is first charged with metal chloride catalyst.

4. The process of claim 3, wherein the metal chloride catalyst is selected from the group comprising $TiCl_4$, $SnCl_4$, $TaCl_5$, $SbCl_3$, $AlCl_3$, $SbCl_5$, and combination thereof.

5. The process of claim 4, wherein the metal chloride catalyst comprises a combination of $SbCl_5$ and $TiCl_4$.

6. The process of claim 1, wherein step (b) further comprises step (b1) removing trace amounts of unsaturated compounds present after step (b).

7. The process of claim 6, wherein step (b1) is conducted using photochlorination.

8. The process of claim 1, wherein step (b) is conducted in a liquid phase reactor.

9. The process of claim 8, wherein the liquid phase reactor is charged with a liquid catalyst which includes solutions or suspensions of metal chlorides such as aluminum chloride, ferric chloride, tin chloride, gallium chloride, cobalt chloride, nickel chloride, zinc chloride, and their various combinations.

10. The process of claim 1, wherein step (b) is conducted in a gas phase reactor.

11. The process of claim 10, wherein the gas phase reactor is charged with a solid catalyst which includes metal chlorides such as aluminum chloride, ferric chloride, tin chloride, gallium chloride, cobalt chloride, nickel chloride, zinc chloride, thorium oxychloride, rare-earth oxides, and their various combinations.

12. The process of claim 1, wherein step (d) is conducted in a liquid phase reactor with a caustic solution.

13. The process of claim 1, wherein step (d) is conducted in the vapor phase using a dehydrochlorination catalyst.

14. The process of claim 13, wherein the dehydrochlorination catalyst is one or more of halogenated metal oxides in bulk form or supported, metal halides in bulk form or supported, and carbon supported transition metals.

15. A process for co-manufacturing 1233zd(E), 1234ze(E), and 245fa which comprises the following steps:
   (a) reacting 1,1,1,3,3-pentachloropropane (HCC-240fa) with hydrogen fluoride in the presence of a fluorination catalyst in a first reactor to form a product stream comprising HCl, HF, and an organic mixture of 1233zd, 1234ze, 244fa, and 245fa;
   (b) separating and recovering HCl and HF from product stream of step (a);
   (c) reacting the organic mixture from step (b) with hydrogen chloride in the presence of a hydrochlorination catalyst in a second reactor to form a product stream comprising 243fa, 244fa, and 245fa;
   (d) separating and recovering HCl from product stream of step (c);
   (e) optionally removing trace amounts of unsaturated compounds present after step (d) by photochlorination;
   (f) separating and purifying 245fa as a first product;
   (g) reacting 243fa and 244fa by dehydrochlorination in a third reactor to form a product stream containing 1233zd and 1234ze;
   (h) separating and recovering HCl from the product stream of step (g);
   (i) separating and purifying 1234ze(E) and 1233zd(E) as a second product and a third product, from the product stream of step (h);
   (j) sending a combined product stream from step (i) which contains 1233zd(Z), 1234ze(Z), 243fa, and 244fa back to the third reactor for a recycle reaction in step (g); and
   (k) optionally reacting 1233zd(Z) and 1234ze(Z) included in the combined product stream from step (i) in the presence of an isomerization catalyst in a fourth reactor to form a product stream containing 1234ze(E) and 1233zd(E) and separating these compounds from the reaction stream before the recycle step.

16. The process of claim 15, wherein step (a) is conducted in a liquid phase reactor.

17. The process of claim 16, wherein the liquid-phase fluorination reactor is first charged with metal chloride catalyst.

18. The process of claim 17, wherein the metal chloride catalyst is selected from the group comprising $TiCl_4$, $SnCl_4$, $TaCl_5$, $SbCl_3$, $AlCl_3$, $SbCl_5$, and combination thereof.

19. The process of claim 18, wherein the metal chloride catalyst comprises a combination of $SbCl_5$ and $TiCl_4$.

20. The process of claim 15, wherein step (g) is conducted in the vapor phase in the presence of a dehydrochlorination catalyst.

21. The process of claim 20, wherein the dehydrochlorination catalyst is one or more of halogenated metal oxides in bulk form or supported, metal halides in bulk form or supported, and carbon supported transition metals.

22. The process of claim 15, wherein step (g) is conducted in a liquid phase with a caustic solution.

23. A process for co-manufacturing 1233zd(E), 1234ze(E), and 245fa which comprises the following steps:
- (a) reacting 1,1,1,3,3-pentachloropropane (240fa) with anhydrous HF in excess in the presence of a catalyst in a liquid-phase reactor to co-produce 1233zd, 1234ze, 244fa, and 245fa, in a first reactor;
- (b) reacting 1233zd and 1234ze with HCl in excess in the presence of a catalyst in a second reactor to convert these two olefins into 243fa and 244fa;
- (c) dehydrochlorinating 243fa and 244fa in a third reactor to form 1233zd and 1234ze; and
- (d) reacting 1233zd(Z) and 1234ze(Z) in the presence of a catalyst in a fourth reactor to form trans-1233zd and trans-1234ze, respectively.

* * * * *